(12) United States Patent
Morgan et al.

(10) Patent No.: US 8,376,938 B2
(45) Date of Patent: Feb. 19, 2013

(54) DISCRETE FLEXION HEAD FOR SINGLE PORT DEVICE

(75) Inventors: Jerome R. Morgan, Cincinnati, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 510 days.

(21) Appl. No.: 12/623,018

(22) Filed: Nov. 20, 2009

(65) Prior Publication Data

US 2011/0124967 A1    May 26, 2011

(51) Int. Cl.
*A61B 1/32* (2006.01)

(52) U.S. Cl. ........................................ 600/204

(58) Field of Classification Search .......... 600/201–209; 604/164.01–164.12, 167.01–167.04
See application file for complete search history.

(56) References Cited

U.S. PATENT DOCUMENTS

| | | | |
|---|---|---|---|
| 3,397,699 | A | 8/1968 | Kohl |
| 4,022,191 | A | 5/1977 | Jamshidi |
| 4,608,977 | A | 9/1986 | Brown |
| 4,809,694 | A | 3/1989 | Ferrara |
| 5,031,634 | A | 7/1991 | Simon |
| 5,053,042 | A | 10/1991 | Bidwell |
| 5,100,387 | A | 3/1992 | Ng |
| 5,201,742 | A | 4/1993 | Hasson |
| 5,235,987 | A | 8/1993 | Wolfe |
| 5,312,417 | A | 5/1994 | Wilk |
| 5,316,014 | A | 5/1994 | Livingston |
| 5,320,111 | A | 6/1994 | Livingston |
| 5,330,437 | A | 7/1994 | Durman |
| 5,342,315 | A | 8/1994 | Rowe et al. |
| 5,431,676 | A | 7/1995 | Dubrul et al. |
| 5,494,039 | A | 2/1996 | Onik et al. |
| 5,569,205 | A | 10/1996 | Hart et al. |

(Continued)

FOREIGN PATENT DOCUMENTS

| | | |
|---|---|---|
| EP | 577400 A1 | 1/1994 |
| WO | 9636283 A1 | 11/1996 |

(Continued)

OTHER PUBLICATIONS

International Search Report and Written Opinion for PCT/US2010/055262 dated Mar. 9, 2011.

(Continued)

*Primary Examiner* — Kevin T Truong
*Assistant Examiner* — Christopher Beccia
(74) *Attorney, Agent, or Firm* — Nutter McClennen & Fish LLP (57) ABSTRACT

Methods and devices are provided for accessing a body cavity. A surgical access device can be configured to be positioned in tissue to provide access through a working channel of the device to a body cavity underlying the tissue. The device can include a flexible member and a plurality of discrete housing portions disposed in at least a proximal portion of an outer housing. Each of the discrete housing portions can be surrounded by the flexible member within the outer housing and be configured to move therein relative to one another and to the outer housing. The flexible member can be configured to act as a barrier between the discrete housing portions such that when one of the discrete housing portions moves, the flexible member can flex to allow the other discrete housing portions to remain in a substantially fixed position relative to the outer housing.

16 Claims, 5 Drawing Sheets

U.S. PATENT DOCUMENTS

| | | | |
|---|---|---|---|
| 5,628,732 A | 5/1997 | Antoon, Jr. et al. | |
| 5,647,373 A | 7/1997 | Paltieli et al. | |
| 5,707,359 A | 1/1998 | Bufalini | |
| 5,743,884 A * | 4/1998 | Hasson et al. | 604/167.02 |
| 5,857,999 A | 1/1999 | Quick et al. | |
| 5,868,673 A | 2/1999 | Vesely | |
| 5,882,340 A | 3/1999 | Yoon | |
| 5,911,707 A | 6/1999 | Wolvek et al. | |
| 5,916,175 A | 6/1999 | Bauer | |
| 5,941,889 A | 8/1999 | Cermak | |
| 5,954,670 A | 9/1999 | Baker | |
| 5,984,930 A | 11/1999 | Maciunas et al. | |
| 6,017,356 A | 1/2000 | Frederick et al. | |
| D422,706 S | 4/2000 | Bucholz et al. | |
| 6,048,321 A | 4/2000 | McPherson et al. | |
| 6,110,182 A | 8/2000 | Mowlai-Ashtiani | |
| 6,162,196 A * | 12/2000 | Hart et al. | 604/167.02 |
| 6,195,577 B1 | 2/2001 | Truwit et al. | |
| 6,203,499 B1 | 3/2001 | Imling | |
| 6,216,029 B1 | 4/2001 | Paltieli et al. | |
| 6,231,565 B1 | 5/2001 | Tovey et al. | |
| 6,231,585 B1 | 5/2001 | Takahashi et al. | |
| 6,236,875 B1 | 5/2001 | Bucholz et al. | |
| 6,245,028 B1 | 6/2001 | Furst et al. | |
| 6,283,942 B1 | 9/2001 | Staehlin et al. | |
| 6,361,499 B1 | 3/2002 | Bates et al. | |
| 6,379,307 B1 | 4/2002 | Filly et al. | |
| 6,400,979 B1 | 6/2002 | Stoianovici et al. | |
| 6,443,960 B1 | 9/2002 | Brabrand et al. | |
| 6,445,943 B1 | 9/2002 | Ferre et al. | |
| 6,468,226 B1 | 10/2002 | McIntyre, IV | |
| 6,475,152 B1 | 11/2002 | Kelly, Jr. et al. | |
| 6,490,467 B1 | 12/2002 | Bucholz et al. | |
| 6,501,981 B1 | 12/2002 | Schweikard et al. | |
| 6,529,765 B1 | 3/2003 | Franck et al. | |
| 6,535,756 B1 | 3/2003 | Simon et al. | |
| 6,539,121 B1 | 3/2003 | Haskell et al. | |
| 6,546,279 B1 | 4/2003 | Bova et al. | |
| 6,547,782 B1 | 4/2003 | Taylor | |
| 6,551,270 B1 * | 4/2003 | Bimbo et al. | 604/93.01 |
| 6,569,120 B1 * | 5/2003 | Green et al. | 604/167.04 |
| 6,665,554 B1 | 12/2003 | Charles et al. | |
| 6,687,531 B1 | 2/2004 | Ferre et al. | |
| 6,723,106 B1 | 4/2004 | Charles et al. | |
| 6,731,966 B1 | 5/2004 | Spigelman et al. | |
| 6,752,812 B1 | 6/2004 | Truwit | |
| 6,770,027 B2 | 8/2004 | Banik et al. | |
| 6,782,288 B2 | 8/2004 | Truwit | |
| 6,783,524 B2 | 8/2004 | Anderson et al. | |
| 6,785,572 B2 | 8/2004 | Yanof et al. | |
| 6,808,492 B2 | 10/2004 | Snyder | |
| 7,021,173 B2 | 4/2006 | Stoianovici et al. | |
| 7,056,329 B2 | 6/2006 | Kerr | |
| 7,076,106 B2 | 7/2006 | Haskell et al. | |
| 7,083,626 B2 | 8/2006 | Hart et al. | |
| 7,163,525 B2 * | 1/2007 | Franer | 604/167.03 |
| 7,371,227 B2 * | 5/2008 | Zeiner | 604/167.03 |
| 7,785,294 B2 * | 8/2010 | Hueil et al. | 604/167.06 |
| 7,951,076 B2 * | 5/2011 | Hart et al. | 600/206 |
| 8,033,995 B2 * | 10/2011 | Cropper et al. | 600/207 |
| 8,137,267 B2 * | 3/2012 | Shelton et al. | 600/203 |
| 8,187,178 B2 * | 5/2012 | Bonadio et al. | 600/208 |
| 8,206,294 B2 * | 6/2012 | Widenhouse et al. | 600/210 |
| 8,226,553 B2 * | 7/2012 | Shelton et al. | 600/208 |
| 2003/0100814 A1 | 5/2003 | Kindlein | |
| 2003/0208207 A1 | 11/2003 | Layer | |
| 2003/0229338 A1 | 12/2003 | Irion et al. | |
| 2004/0082969 A1 | 4/2004 | Kerr | |
| 2004/0185453 A1 | 9/2004 | Myerson et al. | |
| 2004/0230161 A1 | 11/2004 | Zeiner | |
| 2004/0254426 A1 | 12/2004 | Wenchell | |
| 2005/0222582 A1 | 10/2005 | Wenchell | |
| 2006/0149137 A1 | 7/2006 | Pingleton et al. | |
| 2006/0247499 A1 | 11/2006 | Butler et al. | |
| 2006/0247673 A1 * | 11/2006 | Voegele et al. | 606/191 |
| 2007/0185453 A1 | 8/2007 | Michael et al. | |
| 2007/0260121 A1 | 11/2007 | Bakos et al. | |
| 2007/0260273 A1 | 11/2007 | Cropper et al. | |
| 2008/0086080 A1 | 4/2008 | Mastri et al. | |
| 2008/0086167 A1 | 4/2008 | Mastri et al. | |
| 2008/0249373 A1 | 10/2008 | Wenchell | |
| 2008/0255519 A1 * | 10/2008 | Piskun et al. | 604/174 |
| 2009/0005799 A1 | 1/2009 | Franer et al. | |
| 2009/0105659 A1 | 4/2009 | Bettuchi et al. | |
| 2009/0187079 A1 | 7/2009 | Albrecht et al. | |
| 2010/0081863 A1 | 4/2010 | Hess et al. | |
| 2010/0081864 A1 | 4/2010 | Hess et al. | |
| 2010/0081880 A1 * | 4/2010 | Widenhouse et al. | 600/201 |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |

FOREIGN PATENT DOCUMENTS

| | | |
|---|---|---|
| WO | 0041759 A1 | 7/2000 |
| WO | 0062689 A1 | 10/2000 |
| WO | 0108563 A2 | 2/2001 |
| WO | WO-0217800 A2 | 3/2002 |
| WO | 2005097019 A2 | 10/2005 |
| WO | 2005097234 A2 | 10/2005 |
| WO | 2006057982 A2 | 6/2006 |

OTHER PUBLICATIONS

U.S. Appl. No. 12/339,473, filed Mar. 6, 2009, Methods and Devices for Providing Access Into a Body Cavity.

U.S. Appl. No. 12/399,482, filed Mar. 6, 2009, Methods and Devices for Providing Access Into a Body Cavity.

U.S. Appl. No. 12/399,547, filed Mar. 6, 2009, Surgical Access Devices and Methods Providing Seal Movement in Predefined Paths.

U.S. Appl. No. 12/399,625, filed Mar. 6, 2009, Methods and Devices for Providing Access Into a Body Cavity.

U.S. Appl. No. 12/420,146, filed Apr. 8, 2009, Methods and Devices for Providing Access Into a Body Cavity.

U.S. Appl. No. 12/424,213, filed Apr. 15, 2009, Cannula With Sealing Elements.

U.S. Appl. No. 12/478,862, filed Jun. 5, 2009, Flexible Cannula Devices and Methods.

U.S. Appl. No. 12/478,882, filed Jun. 5, 2009, Multi-Planar Obturator With Foldable Retractor.

U.S. Appl. No. 12/479,030, filed Jun. 5, 2009, Retractor With Integrated Wound Closure.

U.S. Appl. No. 12/479,096, filed Jun. 5, 2009, Interlocking Seal Components.

U.S. Appl. No. 12/479,293, filed Jun. 5, 2009, Methods and Devices for Providing Access Through Tissue to Surgical Site.

U.S. Appl. No. 12/512,542, filed Jul. 30, 2009, Methods and Devices for Providing Access Into a Body Cavity.

U.S. Appl. No. 12/512,568, filed Jun. 30, 2009, Methods and Devices for Providing Access Into a Body Cavity.

U.S. Appl. No. 12/635,754, filed Dec. 11, 2009, Methods and Devices for Providing Access Into a Body Cavity.

U.S. Appl. No. 12/635,762, filed Dec. 11, 2009, Methods and Devices for Providing Access Into a Body Cavity.

U.S. Appl. No. 12/635,990, filed Dec. 11, 2009, Methods and Devices for Accessing a Body Cavity.

U.S. Appl. No. 12/636,020, filed Dec. 11, 2009, Inverted Conical Expandable Retractor.

U.S. Appl. No. 12/636,023, filed Dec. 11, 2009, Inverted Concical Expandable Retractor With Coil Spring.

U.S. Appl. No. 12/636,174, filed Dec. 11, 2009, Methods and Devices for Providing Access Through Tissue to a Surgical Site.

U.S. Appl. No. 12/636,184, filed Dec. 11, 2009, Methods and Devices for Providing Access Through Tissue to a Surgical Site.

U.S. Appl. No. 12/636,191, filed Dec. 11, 2009, Methods and Devices for Providing Access Through Tissue to a Surgical Site.

U.S. Appl. No. 12/636,205, filed Dec. 11, 2009, Methods and Devices for Providing Access Through Tissue to a Surgical Site.

U.S. Appl. No. 12/636,232, filed Dec. 11, 2009, Methods and Devices for Providing Access Through Tissue to a Surgical Site.

U.S. Appl. No. 12/479,395, filed Jun. 5, 2009, Methods and Devices for Accessing a Body Cavity Using Surgical Access Device With Modular Seal Components.

* cited by examiner

DISCRETE FLEXION HEAD FOR SINGLE PORT DEVICE

FIELD OF THE INVENTION

The present invention relates to methods and devices for performing surgical procedures, and in particular to methods and devices for accessing a body cavity.

BACKGROUND OF THE INVENTION

Abdominal laparoscopic surgery gained popularity in the late 1980s, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm diameter straight tubular cannula or trocar sleeve is then inserted into the abdominal cavity. A laparoscopic telescope connected to an operating room monitor is used to visualize the operative field, and is placed through a the trocar sleeve. Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. Instruments used for mini-laparoscopic procedures are, however, generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedures. In addition, smaller 2-3 mm incisions may still cause undesirable cosmetic outcomes and wound complications (bleeding, infection, pain, keloid formation, etc.).

Since the benefits of smaller and fewer body cavity incisions are proven, it would be desirable to perform an operation utilizing only a single incision. An umbilicus is well-hidden and the thinnest and least vascularized area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications.

Thus, there is a need for instruments and trocar systems which allow laparoscopic procedures to be performed entirely through the umbilicus or a surgical port located elsewhere while at the same time allowing adjustment of instrument position during the surgical procedure.

SUMMARY OF THE INVENTION

The present invention generally provides methods and devices for providing surgical access into a body cavity. In one embodiment, a surgical access device is provided that includes an outer housing having proximal and distal ends with a lumen extending therethrough, and a plurality of discrete housing portions disposed across the proximal end of the outer housing and spaced a distance apart from one another. Each housing portion has an opening extending therethrough and is in communication with the lumen in the outer housing, and the plurality of housing portions are coupled by a flexible member such that each housing portion is independently movable relative to one another. The flexible member can include a gel, a foam, and/or other material.

The housing portions can have a variety of configurations. For example, each housing portion can include at least one sealing element configured to form at least one of a channel seal when no surgical instrument is disposed therethrough and an instrument seal around a surgical instrument inserted therethrough. For another example, each housing portion can be movable relative to one another in a plane transverse to a longitudinal axis of the outer housing and/or be independently movable in multiple directions relative to one another. In some embodiments, each of the housing portions can be substantially rigid.

The surgical access device can optionally include a retractor configured to attach to and distally extend from the outer housing and to be positioned within an opening in tissue. The retractor has a working channel extending therethrough for forming a pathway through tissue into a body cavity. When the retractor is attached to the outer housing, each of the discrete housing portions can be movable relative to the retractor. The retractor can have a variety of configurations, such as including a flexible elongate cannula extending between a proximal ring member and a distal ring member.

In another embodiment, a surgical access device is provided that includes an annular ring defining a lumen, a plurality of discrete housing portions disposed within the ring and defining channels between each of the housing portions, and a flexible member disposed in the channels such that each of the housing portions can move relative to one another in a plane transverse to a longitudinal axis of the ring. Each housing portion has at least one sealing port configured to receive an instrument inserted therethrough and into the lumen. Each sealing port can include at least one sealing element configured to form at least one of a channel seal when no surgical instrument is disposed therethrough and an instrument seal around a surgical instrument inserted therethrough.

The device can vary in any number of ways. The channels can be configured to prevent any of the housing portions from directly contacting one another. Each of the housing portions can be in a longitudinally fixed position relative to the annular ring. The flexible member can provide a fluid-tight seal for the lumen. In some embodiments, the device can include a retractor distally extending from the annular ring and configured to be positioned within an opening in tissue. The retractor can have a working channel extending therethrough for forming a pathway through tissue into a body cavity.

In another aspect, a method is provided for providing access through tissue to a body cavity. The method can include positioning a retractor in an opening in tissue of a patient such that a distal end of the retractor is positioned in a body cavity underlying the tissue. The retractor has an annular ring coupled to a proximal end thereof, and the annular ring defines a lumen. The method can also include inserting an instrument into the body cavity through one of a plurality of discrete housing portions disposed in the lumen of the annular ring such that none of the discrete housing portions directly contact one another, and laterally moving the instrument relative to the annular ring, thereby moving the one of the housing portions relative to each of the other housing portions. Laterally moving the instrument relative to the annular ring can flex a flexible member disposed between the housing portions.

The method can have any number of variations. For example, each of the other housing portions can remain substantially stationary relative to the one of the housing portions when the instrument is laterally moved.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are disclosed for providing access through tissue to a surgical site. In general, a surgical access device is provided that can be configured to be positioned in tissue to enable access through a working channel of the surgical access device to a body cavity underlying the tissue. The surgical access device can include a flexible member and a plurality of discrete housing portions disposed in at least a proximal portion of an outer housing. Each of the discrete housing portions can be surrounded by the flexible member within the outer housing and be configured to move independently therein relative to one another and to the outer housing. The flexible member can be configured to act as a barrier between the discrete housing portions such that when one of the discrete housing portions moves, the flexible member can flex to allow the other discrete housing portions to remain in a substantially fixed position relative to the outer housing. In this way, a surgical instrument inserted through one of the discrete housing portions and into a body cavity can be desirably positioned without disturbing positions of any other instruments inserted through any of the other discrete housing portions.

The various surgical access devices can include a wound protector, cannula, or other member for forming a pathway through tissue (hereinafter generally referred to as a retractor). The retractor can extend from the housing and it can be configured to be positioned within an opening in a patient's body, such as the umbilicus. The sealing ports can each define working channels extending through the housing and aligned with the retractor. Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

As discussed further below, any and all embodiments of a surgical access device can also include one or more retractor protectors or safety shields positioned through, in, and around any of the components and/or tissue to protect the components against puncture or tear by surgical instruments being inserted through the device. In addition, any and all embodiments of a surgical access device can include engagement and release mechanisms that allow certain components of the surgical access device to be removable as needed.

In use, and as also further discussed below, the surgical access devices disclosed herein can provide access to a patient's body cavity. The retractor can be positionable within an opening in a patient's body such that a distal portion of the retractor extends into a patient's body cavity and a proximal portion configured to couple to the housing is positioned adjacent to the patient's skin on an exterior of the patient's body. A lumen in the retractor can form a pathway through the opening in a patient's body so that surgical instruments can be inserted from outside the body to an interior body cavity. The elasticity of the skin of the patient can assist in the retention of the retractor in the body opening or incision made in the body. The retractor can be placed in any opening within a patient's body, whether a natural orifice or an opening made by an incision. In one embodiment, the retractor can be substantially flexible so that it can easily be maneuvered into and within tissue as needed. In other embodiments, the retractor can be substantially rigid or substantially semi-rigid. The retractor can be formed of any suitable material known in the art, e.g., silicone, urethane, thermoplastic elastomer, and rubber. Non-limiting examples of retractors include a Hakko® Wound Protector available from Hakko Medical Co. of Tokyo, Japan, an Alexis® Wound Protector available from Applied Medical Resources Corp. of Rancho Santa Margarita, Calif., and a Mobius® Retractor available from Apple Medical Corp. of Marlborough, Mass. In some embodiments, discussed further below, a retractor is not positioned outside a patient's body. Rather, a proximal portion of a surgical access the retractor can be positionable within an opening in a patient's body such that a proximal end of the device is positioned adjacent to the patient's skin on an exterior of the patient's body and a retractor distally extending from the proximal portion of the device is positioned within the opening and/or within a patient's body cavity.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough, at least one channel seal or zero-closure seal that seals the working channel created by the sealing port when no instrument is disposed therethrough, or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment.

Figure 1:
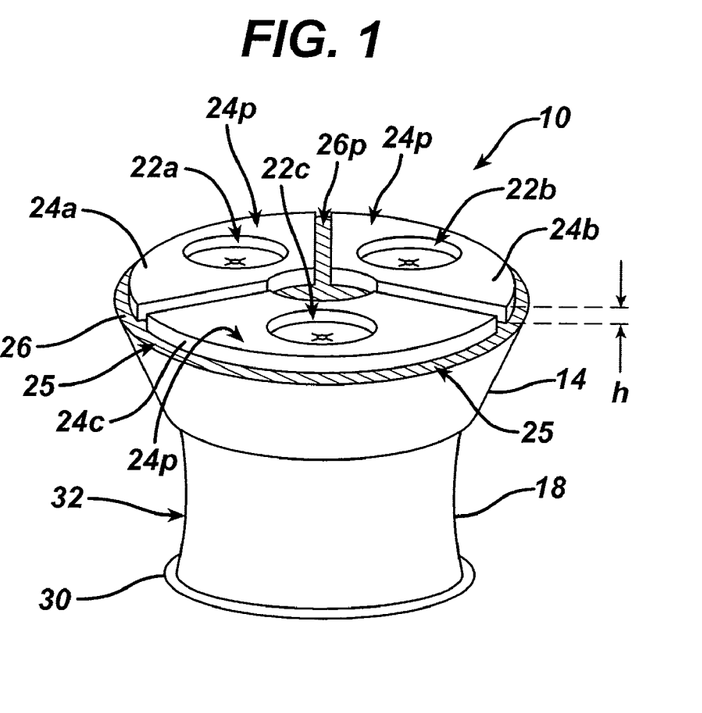
FIG. 1 is a perspective view of one embodiment of a surgical access device including a plurality of discrete housing portions.
Figure 2:
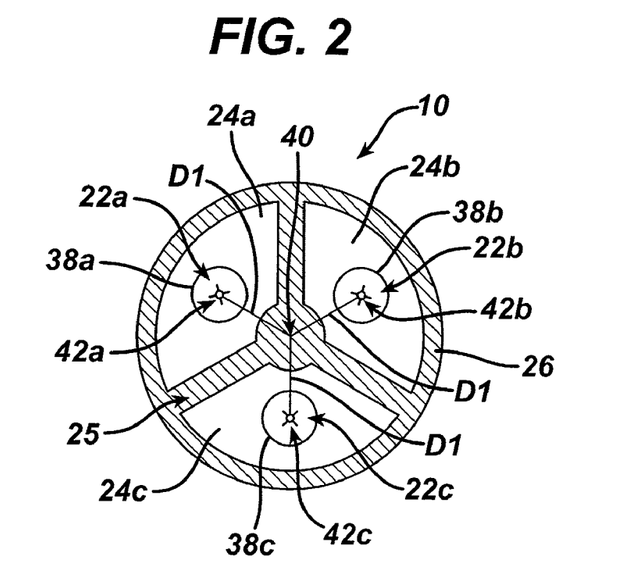
FIG. 2 is a top view of the surgical access device of FIG. 1.
Figure 3:
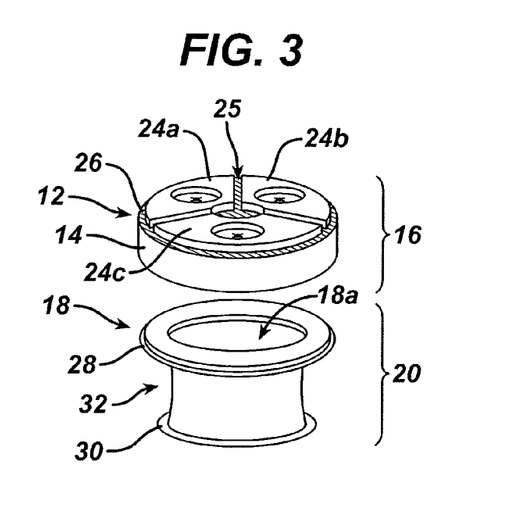
FIG. 3 is an exploded view of the surgical access device of FIG. 1.

In an exemplary embodiment, shown in FIGS. 1-3, a surgical access device 10 is provided having a proximal portion 16 including a housing 12, and a distal portion 20 including a retractor 18 having a pathway, passageway, inner lumen, or working channel 18a extending therethrough. As shown in the illustrated embodiment, the housing 12 can be configured to have one or more surgical instruments inserted therethrough and can include an outer housing 14 having a plurality of discrete housing portions 24a, 24b, 24c, generally referred to as "housing portions," disposed therein that each define at least one sealing or access port. While the housing 12 can have any number of discrete housing portions, in the illustrated embodiment, first, second, and third housing portions 24a, 24b, 24c are disposed in the outer housing 14. Although each of the housing portions 24a, 24b, 24c can seat any number of sealing ports, in the illustrated embodiment the first, second, and third housing portions 24a, 24b, 24c have first, second, and third sealing ports 22a, 22b, 22c, respectively, that extend through the outer housing 14 and that respectively seat first, second, and third sealing elements, as discussed further below. A flexible member 26 disposed in the outer housing 14 can couple together the housing portions 24a, 24b, 24c and be configured to allow each of the housing portions 24a, 24b, 24c to freely, independently move relative to one another, as discussed further below. The housing 12 can be configured to releasably or fixedly mate to the retractor 18. The retractor 18 can thus be configured to distally extend from the housing 12 and to provide a pathway through tissue into a body cavity. In the embodiment shown, the retractor 18 is flexible and has a proximal flange 28 and a distal flange 30 with an inner elongate portion 32 extending therebetween. The housing 12 and the retractor 18 can each have various sizes, shapes, and configurations, as discussed further below.

A person skilled in the art will appreciate that the device 10 can include any number of other elements, such as an intermediate locking ring (not shown) disposed between the housing 12 and the retractor 18 and configured to facilitate releasable attachment of the housing 12 and the retractor 18, and such as an o-ring (not shown) configured to provide a seal between two or more elements.

The device 10 can also include an insufflation port (not shown) in the outer housing 14, although a person skilled in the art will appreciate that the insufflation port can be located elsewhere in the housing 12 or in other locations, e.g., in the flexible member 26, in one of the housing portions 24a, 24b, 24c, etc. A person skilled in the art will also appreciate that the device 10 can include any number of insufflation ports and that an insufflation port can have a variety of configurations. Generally, the insufflation port can be configured to pass an insufflation fluid through a flexible insufflation tube and into an insufflation orifice of the insufflation port where the fluid can flow through a pathway, inner lumen, passageway, or working channel 14a defined by the outer housing 14, into the retractor's pathway 18a, and into a body cavity. A stopcock can control fluid flow through the insufflation tube.

The retractor 18 can have various sizes, shapes, and configurations. Although the retractor 18 in the illustrated embodiment is flexible, as mentioned above the retractor 18 can be rigid. As also mentioned above, the retractor 18 can extend distally from the proximal portion 16 of the device 10, and it can be configured to be positioned in an opening formed in tissue. The inner elongate portion 32 of the retractor 18 can, as shown in FIG. 3, have a diameter less than a diameter of the proximal and distal flanges 28, 30, which can have the same diameter or different diameters from one another. The proximal flange 28 can be configured to be seated within the outer housing 14, such as on a distal flange (not shown) extending radially inward at a distal end of the outer housing 14, and be optionally attached thereto using an adhesive, sealant, complementary threads, or any other attachment mechanism, as will be appreciated by a person skilled in the art. A proximal o-ring (not shown) can be optionally positioned within the proximal flange 28 to help provide structural support to the retractor 18 within the outer housing 14. A distal o-ring (not shown) can optionally be positioned within the distal flange 30 to provide structural support to the retractor 18 within a patient's body. The proximal and distal o-rings can be substantially flexible or substantially rigid as needed for use in a particular application.

The housing 12 of the surgical access device 10 can have a variety of sizes, shapes, and configurations. The housing 12 in the illustrated embodiment is non-removably attached to the retractor 18 and is not rotatable or otherwise movable relative thereto, except for flexing of the flexible member 26 and movement of the housing portions 24a, 24b, 24c as discussed further below. However, in some embodiments, the housing 12 can be movable relative to the retractor 18, e.g., the housing 12 can be configured to be releasable from and reattachable to the retractor 18, the housing 12 can be configured to rotate relative to the retractor 18, etc. Exemplary embodiments of housings releasable from and reattachable to a retractor and/or rotatable relative to a retractor are described in more detail in U.S. patent application Ser. No. 12/399,473 entitled "Methods And Devices For Providing Access Into A Body Cavity," filed on Mar. 6, 2009, U.S. Patent Application No. 2006/0247673 entitled "Multi-port Laparoscopic Access Device" filed Nov. 2, 2006, U.S. application Ser. No. 12/399,482 entitled "Methods and Devices for Providing Access to a Body Cavity" filed on Mar. 6, 2009, U.S. application Ser. No. 12/242,765 entitled "Surgical Access Device" filed on Sep. 30, 2008, U.S. application Ser. No. 12/512,542 entitled "Methods And Devices For Providing Access Into A Body Cavity" filed on Jul. 30, 2009, and U.S. application Ser. No. 12/512,568 entitled "Methods And Devices For Providing Access Into A Body Cavity" filed on Jul. 30, 2009, which are hereby incorporated by reference in their entireties.

In any and all of the surgical access device embodiments disclosed herein, an engagement and/or release mechanism can be included to allow the housing 12 to be separated from the retractor 18, and/or to allow a sealing element to be removed from any of the housing portions 24a. 24b. 24c. Any engagement and release mechanism known in the art, e.g., a snap-lock mechanism, corresponding threads, etc., can be used to releasably mate two components of the device 10. In an exemplary embodiment, the engagement and release mechanism can include a latch mechanism, as described by way of non-limiting example in U.S. application Ser. No. 12/242,765 entitled "Surgical Access Device" filed on Sep. 30, 2008, which is hereby incorporated by reference in its entirety. In another exemplary embodiment, the engagement and release mechanism can include a bayonet latch mechanism, as described by way of non-limiting example in U.S. application Ser. No. 12/242,765 entitled "Surgical Access Device" filed on Sep. 30, 2008, U.S. application Ser. No. 12/399,482 entitled "Methods and Devices for Providing Access to a Body Cavity" filed on Mar. 6, 2009, U.S. application Ser. No. 12/512,542 entitled "Methods And Devices For Providing Access Into A Body Cavity" filed on Jul. 30, 2009, and U.S. application Ser. No. 12/512,568 entitled "Methods And Devices For Providing Access Into A Body Cavity" filed on Jul. 30, 2009, which are hereby incorporated by reference in their entireties.

The housing 12 can include, as illustrated in FIGS. 1-4, the outer housing 14, the flexible member 26, and the housing portions 24a, 24b, 24c. The outer housing 14 can include an annular ring, e.g., a substantially rigid cylindrical or circular member, that defines the working channel 14a extending therethrough between proximal and distal ends 14p, 14d of the outer housing 14. The flexible member 26 and the housing portions 24a, 24b, 24c can be disposed across the proximal end 14p of the outer housing 14 to define a proximal surface of the housing 12. Although the flexible member 26 and the housing portions 24a, 24b, 24c can be configured to be removable from the outer housing 14 as a singular unit as shown in the exploded view of the housing 12 in FIG. 4, the flexible member 26 and the housing portions 24a, 24b, 24c in the illustrated embodiment are non-removably attached to the outer housing 14. The flexible member 26 and the housing portions 24a, 24b, 24c can together provide a fluid-tight seal of the outer housing's working channel 14a. A person skilled in the art will appreciate that one or more seal members, e.g., o-rings (not shown), can be positioned between the outer housing 14 and the flexible member 26 and/or the housing portions 24a, 24b, 24c to help form a seat and seal therebetween.

The flexible member 26 can have a variety of configurations. The flexible member 26 can be formed of any one or more materials in any combination. Generally, the material can include a flexible, composite material, e.g., a gel, a foam, an elastomer, isoplast (polyurethane), polyisoprene (natural rubber), santoprene (thermoplastic rubber), etc., configured to prevent fluid passage therethrough, to flex upon application of an external force without breaking, tearing, or otherwise allowing fluid to pass therethrough, and to dynamically flex to return to a default or resting position when the external force is removed. While a person skilled in the art will appreciate that any gel material can be used, a non-limiting example of a gel material includes a combination of an internal low molecular weight chemical species such as mineral oil or other oil, plasticizer, etc. and Kraton™ Rubber, e.g., styrene-ethylene/butylene-styrene (S-E/B-S) tri-block polymer, available from Kraton Polymers LLC of Houston, Tex. Generally, a foam material can have a lower elastic modulus than a gel material, e.g., about 10% of the elastic modulus of a gel material. While a person skilled in the art will also appreciate that any foam material can be used, non-limiting examples of a foam material includes Kraton™ Rubber, silicone elastomers, polyurethanes, polyolefins such as polypropylene and polyethylene, polyolefin elastomers such as Santoprene™, e.g., a crosslinked co-polymer of polypropylene and EPDM (ethylene propylene diene M-class) rubber, available from Advanced Elastomer Systems, LP of Akron, Ohio, polyethylene-co-vinyl acetate copolymers, polytetrafluoroethylene (PTFE) in the form of expanded PTFE, etc. The flexible material 26 can optionally have a protective coating (not shown) on at least a proximal surface thereof to help prevent damage to the flexible material 26 from sharp instruments or other objects.

In some embodiments, the flexible material 26 can be configured to allow one or more surgical instruments to be inserted therethrough and to form an instrument seal around the instrument(s) inserted therethrough. Exemplary embodiments of a flexible material through which instruments can be inserted are described in more detail in U.S. patent application Ser. No. 12/479,293 entitled "Methods And Devices For Providing Access Through Tissue To A Surgical Site", filed on Jun. 5, 2009, which is hereby incorporated by reference in its entirety.

The flexible material 26 can be configured to have the housing portions 24a, 24b, 24c disposed, seated, or suspended therein and to form a seat and seal between the housing 12 and a distal portion of the device 10, e.g., the retractor 18. Generally, each of the housing portions 24a, 24b, 24c can be disposed in the flexible material 26 with the flexible member 26 acting as a hinge and providing a barrier between each of the housing portions 24a, 24b, 24c such that none of the housing portions 24a, 24b, 24c directly contact one another. In other words, the housing portions 24a, 24b, 24c can be disposed in the outer housing's working channel 14a and define channels 25 therebetween in which the flexible material 26 can be disposed. The flexible material 26 can be disposed in the channels 25 defined by and extending between the housing portions 24a, 24b, 24c and the outer housing 14.

The channels 25 can, as shown in the illustrated embodiment, extend between each of the housing portions 24a, 24b, 24c and around an inner perimeter or circumference of the outer housing 14 such that the flexible member 26 is contained within the outer housing 14 and surrounds each of the housing portions 24a, 24b, 24c to prevent any of the housing portions 24a, 24b, 24c from being in direct contact with the outer housing 14. With the flexible member 26 surrounding a perimeter or circumference of each of the housing portions 24a, 24b, 24c, the housing portions 24a, 24b, 24c can freely and selectively move in any direction relative to one another and to the outer housing 14, as discussed further below. In this way, fluid cannot pass from outside the device 10 and into the retractor 18 or vice versa when the device 10 is positioned in an opening in tissue. The flexible material 26 can be configured to maintain a seat and seal between the housing 12 and the retractor 18 when any one or more of the housing portions 24a, 24b, 24c so move, e.g., maintain a substantially closed space between the moving one or more housing portions 24a, 24b, 24c and the flexible member 26.

The housing portions 24a, 24b, 24c can each have any size, shape, and configuration, as can the sealing ports 22a, 22b, 22c. Generally, the housing portions 24a, 24b, 24c include discrete, separate, isolated, or non-contacting units each being sealed relative to one another such that a surgical instrument inserted through one housing portion does not disturb channel and/or instrument seals provided by the flexible member 26 and by the other housing portions. The housing portions 24a, 24b, 24c can be disposed in the flexible member 26 such that proximal surfaces 24p of the housing portions 24a, 24b, 24c can extend above or proximally beyond a proximal surface 26p of the flexible member by a distance or height h. Positioning at least a portion of the housing portions 24a, 24b, 24c above the flexible member 26 can help improve accessibility of the housing portions 24a, 24b, 24c when the device 10 is positioned in tissue. In some embodiments, the proximal surfaces 24p of any one or more of the housing portions 24a, 24b, 24c can be flush or co-planar with the proximal surface 26p of the flexible member 26 and/or be recessed within the flexible member 26.

The housing portions 24a, 24b, 24c can be radially arranged around a central axis or center point of the housing 12, e.g., a central axis or center point 40 of the outer housing 14, such that each of the sealing ports 22a, 22b, 22c can have a central axis or center point 42a, 42b, 42c that differs from each other. Each of the sealing ports 22a, 22b, 22c can have center points 42a, 42b, 42c selectively positioned any distance from the center point 40 of the outer housing 14. When the housing 12 is in a default or resting configuration such that the flexible member 26 is not flexing and the housing portions 24a, 24b, 24c are in default or resting positions, the center points 42a, 42b, 42c of the sealing ports 22a, 22b, 22c can each be located a same first distance D1 from the outer housing's center point 40. When one of the housing portions 24a, 24b, 24c moves relative to the outer housing 14 and to the other housing portions 24a, 24b, 24c to move from the default position to an offset position, the center point 42a, 42b, 42c of the moving housing portion 24a, 24b, 24c changes, and hence the first distance D1 changes.

As mentioned above, each of the housing portions 24a, 24b, 24c can be movably disposed in the outer housing's working channel 14a and be configured to move relative to the outer housing 14, to one another, and to the retractor 18. Generally, any one of the housing portions 24a, 24b, 24c can be selectively, laterally moved in any one or more direction toward and/or away from any of the other housing portions 24a, 24b, 24c. Such a configuration can help facilitate instrument positioning in a body cavity to which the device 10 provides access and can help prevent jostling or otherwise moving a previously-positioned instrument inserted through another one of the housing portions 24a, 24b, 24c. Because the flexible member 26 surrounds each of the housing portions 24a, 24b, 24c, the housing portions 24a, 24b, 24c are each free to move in any direction 360° therearound.

Figure 5:
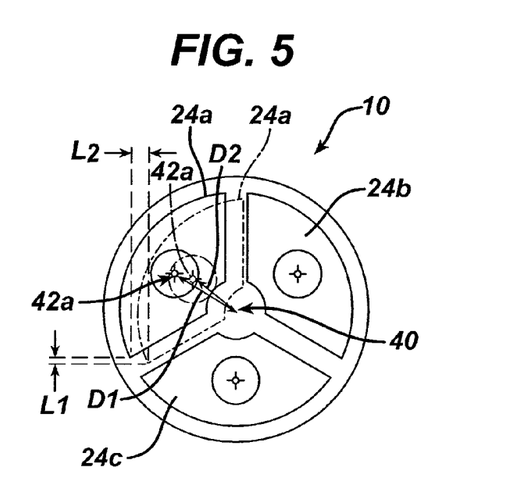
FIG. 5 is a top view of the surgical access device of FIG. 1 showing movement of one of the discrete housing portions relative to other discrete housing portions.
Figure 15:
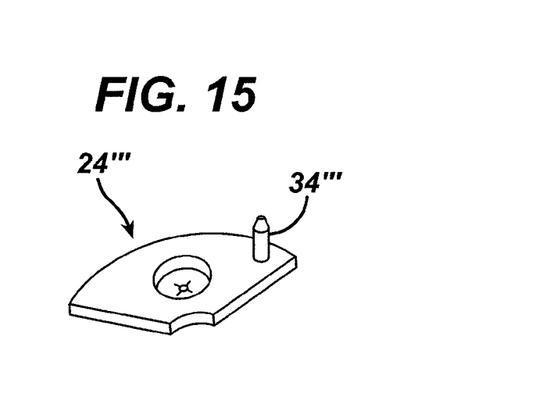
FIG. 15 is a perspective view of one embodiment of a discrete housing portion having an insufflation port extending therefrom.

As shown by way of non-limiting example in FIG. 15, the first housing portion 24a can be moved relative to the second and third housing portions 24b, 24c and the outer housing 14 from a first position, shown with the first housing portion 24a in solid outline, to a second position, shown with the first housing portion 24b in dotted outline, relative to the second and third housing portions 24b, 24c and the outer housing 14. When the first housing portion 24a moves, the flexible member 26 flexes, e.g., stretches and compresses, in the channels 25, thereby allowing movement of the first housing portion 24a while holding the other housing portions 24b, 24c in substantially fixed positions relative to the first housing portion 24a and the outer housing 14. Maintaining the second and third housing portions 24b, 24c in substantially fixed positions while the first housing portion 24a moves and when the first housing portion 24a is in the second, non-default position can allow any instruments inserted through the second and/or third housing portions 24b, 24c to remain in desired positions. From the first position to the second position the first housing portion 24a has been moved radially inward in two directions such that the first housing portion 24a has moved a first lateral distance L1 in a downward direction and a second lateral distance L2 in a right direction. A person skilled in the art will appreciate that "downward" and "right" are relative directions for the perspective view in FIG. 5 and that the housing portions 24a, 24b, 24c can each move in any lateral direction, i.e., in a plane transverse to a longitudinal axis of the device 10, e.g., the central axis of the outer housing 40. The first housing portion's center point 42a is the first distance D1 from the outer housing's center point 40 with the first housing portion 24a in the first position and changes to a second distance D2 with the first housing portion 24a in the second position. The second distance D2 is smaller than the first distance D1 in the illustrated embodiment, but the second distance D2 can be greater than the first distance D1. Moreover, although the first distance D1 changed between the first and second positions in the illustrated embodiment, the first housing portion 24a can move from the first position to another position in an orbit around the outer housing's center point 40 such that the first distance D1 remains constant. As mentioned above, although the first housing portion 24a is shown in FIG. 5 to have moved radially inward from the first position to the second position, the first housing portion 24a can be moved in any direction. A person skilled in the art will also appreciate that while FIG. 5 illustrates the first housing portion 24a moving between only two positions, the first housing portion 24a, as well as any or all of the other housing portions 24b, 24c, can be repositioned any number of times and in any number of directions. The housing portions 24a, 24b, 24c can simultaneously and/or sequentially move relative to each other and the outer housing 14.

Although in the illustrated embodiment the housing portions 24a, 24b, 24c are configured to only be laterally movable, e.g., movable in a plane of the housing's proximal surface, in some embodiments the housing portions 24a, 24b, 24c can be configured to be additionally or alternatively longitudinally movable relative to the outer housing 14. In other words, the housing portions 24a, 24b, 24c of FIGS. 1-4 can horizontally move relative to the outer housing 14 and the retractor 18 but cannot vertically move relative to the outer housing 14 and the retractor 18. A person skilled in the art will appreciate that the housing portions 24a, 24b, 24c can have negligible vertical movement in the illustrated embodiment but nevertheless generally have substantially fixed vertical positions relative to the outer housing 14. If vertical repositioning of a surgical instrument inserted through one of the housing portions 24a, 24b, 24c is desired, the instrument can be vertically moved relative to the one of the housing portions 24a, 24b, 24c.

Although the housing portions 24a, 24b, 24c can be configured to be movable relative to the outer housing 14 and the retractor 18 through application of an external force with or without any instruments inserted through any of their respective sealing ports 22a, 22b, 22c, e.g., by being manually moved by hand, the housing portions 24a, 24b, 24c can also be configured to move relative to the outer housing 14 and the retractor 18 in response to motion of at least one instrument inserted through one of the sealing ports 22a, 22b, 22c. When the external force is removed from a moved one of the housing portions 24a, 24b, 24c, the moved one of the housing portions 24a, 24b, 24c can return to its default position.

Figures 4, 6:
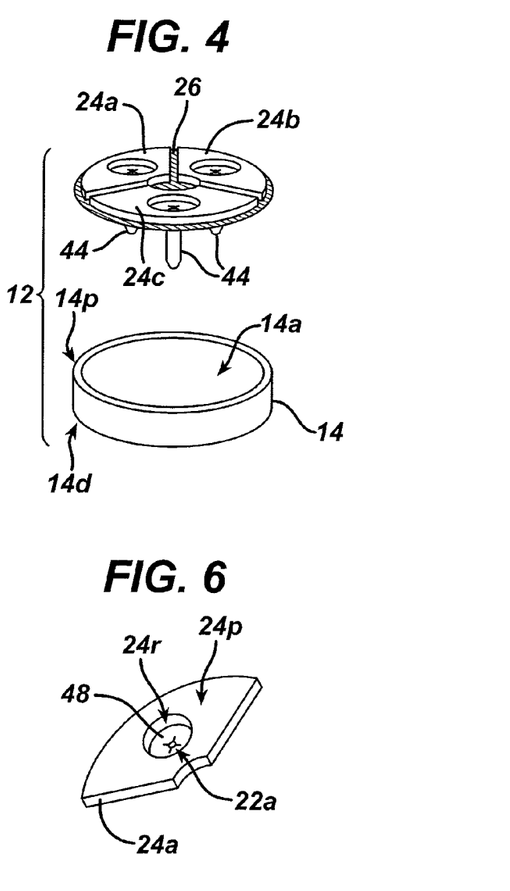
FIG. 4 is an exploded view of a housing of the surgical access device of FIG. 1.
FIG. 6 is a perspective view of one of the discrete housing portions of the surgical access device of FIG. 1.
Figure 7:
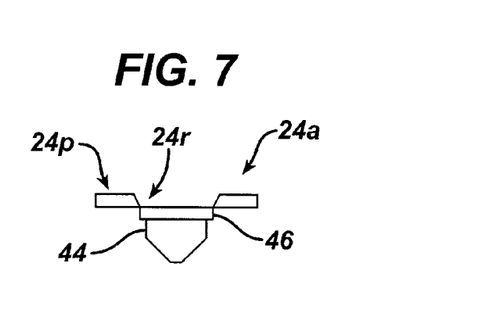
FIG. 7 is a side, cross-sectional view of the discrete housing portion of FIG. 6.
Figure 8:
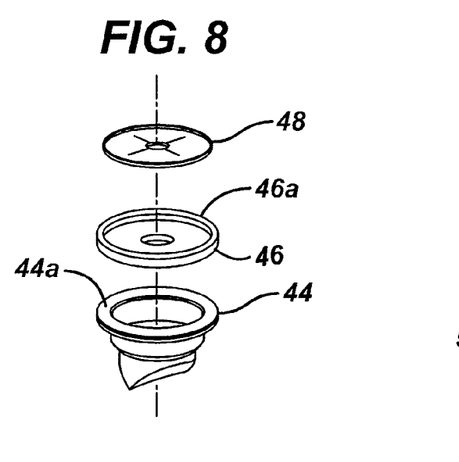
FIG. 8 is an exploded view of one embodiment of a sealing element.

As shown in FIGS. 1-4, 6, and 7, the housing portions 24a, 24b, 24c can each be wedge-shaped and include first, second, and third cut-outs or openings 38a, 38b, 38c that define the first, second, and third sealing ports 22a, 22b, 22c, respectively. The housing portions 24a, 24b, 24c can have other shapes, e.g., cylindrical. In some embodiments, a proximal surface of a housing portion can be substantially flat with the housing portion's port opening being formed in a same plane with each other, either co-planar parallel to the proximal surface or recessed in the housing portion. Alternatively, a proximal surface 24p of the first housing portion 24a can be non-planar with at least one raised portion proximally displaced from and substantially parallel to a plane of the proximal surface 24p, or, as shown in FIGS. 6 and 7 illustrating the first housing portion 24a, with at least one recessed portion 24r extending in a plane distally displaced from and substantially parallel to a plane of the proximal surface 24p. The housing portion's one or more recessed portions and one or more raised portions can help compensate for sealing elements of different lengths to help prevent distal seal element openings of each of the sealing elements from contacting an interior of the retractor 18, at least when the surgical access device 10 is in a default position, e.g., as illustrated in FIGS. 1 and 2, and at least when the device 10 is not positioned in tissue and has no surgical instruments inserted therethrough.

The openings 38a, 38b, 38c can extend through their respective housing portions 24a, 24b, 24c such that surgical instruments can be inserted into the openings 38a, 38b, 38c and into the retractor 18. Although each housing portion 24a, 24b, 24c includes one opening 38a, 38b, 38c, a person skilled in the art will appreciate that a housing portion can include any number of openings arranged in any way, with each opening having at least one associated sealing port. The openings 38a, 38b, 38c can also have any combination of sizes and shapes. As shown, the openings 38a, 38b, 38c can each have a shape corresponding to a shape of the sealing element seated therein, which in the illustrated embodiment is substantially circular. Although the sealing ports 22a, 22b, 22c can have different sizes, e.g., 3 mm, 5 mm, 15 mm, 12 mm, etc., in the illustrated embodiment, the openings 38a, 38b, 38c have equal sizes and have equal-sized sealing ports 22a, 22b, 22c seated therein.

As shown in the illustrated embodiment, each of the sealing ports 22a, 22b, 22c can each have a central axis, e.g., a longitudinal axis through their respective center points 42a, 42b, 42c, that extends substantially perpendicular to a plane of the proximal surface 14p of the outer housing 14 and that is substantially parallel to a longitudinal axis of the retractor 18. The sealing ports 22a, 22b, 22c can each be in a fixed position relative to their respective housing portions 24a, 24b, 24c as in the illustrated embodiment such that center axes of the sealing ports 22a, 22b, 22c are substantially perpendicular to proximal surfaces 24p of their respective housing portions 24a, 24b, 24c, but any one or more components in each sealing port can be angled relative to its respective housing portion 24a, 24b, 24c and/or rotatable or otherwise movable relative to its respective housing portion 24a, 24b, 24c and/or other portion(s) of the housing 12.

In general, each of the sealing ports 22a, 22b, 22c can include a sealing element providing an instrument seal and/or a channel or zero-closure seal disposed therein. The sealing elements disposed in each sealing port 22a, 22b, 22c can be attached or mated to their respective housing portions 24a, 24b, 24c using any attachment or mating mechanism known in the art. In the illustrated embodiment, each sealing element is engaged by an interference fit between upper and lower portions (not shown) of its respective housing portion 24a, 24b, 24c. Although the housing portions 24a, 24b, 24c can each be a singular member or can have multiple portions mated together in any way, in an exemplary embodiment, pins can proximally extending from an outer perimeter of a housing portion's lower portion and be configured to extend into corresponding bores formed in a circumferential wall of the housing portion's upper portion to mate the upper and lower portions together.

The sealing elements can have a variety of sizes, shapes, and configurations. As shown in the illustrated embodiment in FIGS. 4, 6, 7, and 8, the sealing elements of the housing portions 24a, 24b, 24c each include a distal duckbill seal 44 that provides a channel seal, and a proximal septum seal 46 that provides an instrument seal. A protective member 48 can be positioned proximal to the septum seal 46 to protect the septum seal 46 from accidental puncture. The septum seal 46 can optionally include a beveled edge on an interior circumference thereof, which can help facilitate instrument insertion therethrough. If the septum seal 46 has an interior beveled edge, the protective member 48 can have an inner diameter substantially equal to an outer diameter of the beveled circumferential edge, which can help protect the septum seal 46 without floating and without substantially limiting angular movement of instruments inserted therethrough. The duckbill seal 44 forms a channel or zero-closure seal to seal a working channel of the sealing port when no instrument is disposed therethrough to prevent leakage of insufflation gases delivered through the surgical access device 10 to a body cavity. The duckbill seal 44 will generally not form a seal around an instrument inserted therethrough. In use, when a surgical instrument is passed through one of the sealing ports 22a, 22b, 22c through a center opening of the protective member 48 and the septum seal 46, the septum seal 46 can engage and form a seal around an outer surface of the instrument to thereby prevent the passage of fluids and gas through the seal. When no instrument is disposed therethrough, the center opening of the protective member 48 and the septum seal 46 will generally not form a seal in the working channel of sealing port. A person skilled in the art will appreciate that while instrument seals in the form of septum seals are shown, any seal can be used and can be aligned in any way relative to its associated housing portion 24a, 24b, 24c and to the outer housing 14. Exemplary instrument seal configurations are described in more detail in U.S. Patent Publication No. 2004/0230161 entitled "Trocar Seal Assembly," filed on Mar. 31, 2004, and U.S. patent application Ser. No. 10/687,502 entitled "Conical Trocar Seal," filed on Oct. 15, 2003, which are hereby incorporated by reference in their entireties. When the instrument is further inserted through the duckbill seal 44, the instrument can open the duckbill seal 44 and pass into the working channel 18a of the retractor 18 when the retractor 18 is coupled to the housing 12. Although the first, seconds and third sealing elements of the first, second, and third housing portions 24a, 24b, 24c are identical to one another in the illustrated embodiment, a person skilled in the art will appreciate that the second and third sealing elements can be same as or different from any one or more of the other sealing elements.

Figure 9:
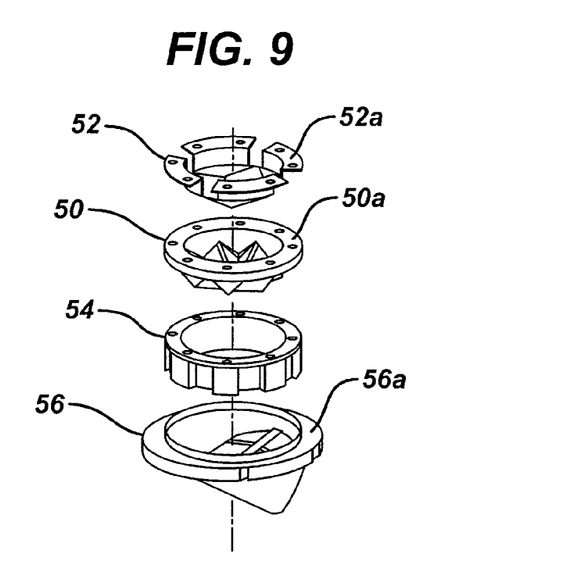
FIG. 9 is an exploded view of another embodiment of a sealing element.

FIG. 9 illustrates another exemplary embodiment of a sealing element that can be included in a housing portion. This sealing element includes a fan seal 50, a fan seal protector 52 positioned concentric with and proximal to the fan seal 50, and a bottom ring 54 in which the fan seal 50 can be concentrically seated with the fan seal protector 52 to together form an instrument seal in a sealing port. A distal duckbill seal 56 can be positioned concentric and distal to the bottom ring 54, and thus the bottom ring 54 can act as a spacer to separate the fan seal 50 and the duckbill seal 62. The sealing element of FIG. 9 can generally be used in a manner similar to the sealing element of FIG. 8, with an instrument being insertable through a center opening in the fan seal 50 and the fan seal protector 52 and then through the duckbill seal 56 and into a working channel of the retractor 18 when the retractor 18 is coupled to the housing 12.

Each of the distal duckbill seals 44, 56, the fan seal 50, the fan seal protector 52, and the septum seal 46 can include a radially-outward extending proximal flange 44a, 46a, 50a, 52a, 56a. The proximal flanges 44a, 46a, 50a, 52a, 56a can each be captured between a proximal surface of the lower portion of a housing portion and an inner distal cylindrical rib or projection formed around each of the openings in the upper portion of the housing portion, thereby seating the sealing elements within their respective port openings in the housing portion. As noted above, however, the sealing element of FIG. 9 includes the bottom ring 54 and the sealing element of FIG. 8 includes the protective member 48 that are also captured between upper and lower portions of a housing portion. The upper and lower portions of the housing portions 24a, 24b, 24c can be sealingly engaged, thereby forming a seal around the sealing ports 22a, 22b, 22c. To seal together, one or more projections, e.g., cylindrical pegs or prongs (not shown), can proximally extend from an inner surface of a housing portion's lower portion and each be inserted into a corresponding cavity (not shown), e.g., a cylindrical bore, formed in an inner surface of the housing portion's upper portion.

A person skilled in the art will appreciate that while channel or zero-closure seals in the form of duckbill seals are shown for the distal seals 44, 56, any seal, e.g., duckbill seals, cone seals, flapper valves, gel seals, diaphragm seals, lip seals, iris seals, non-linear sealing elements such sealing elements with an S-shaped opening, etc., same or different from any other of the other distal seals 44, 56 can be used and can be aligned in any way relative to their respective housing portions 24a, 24b, 24c and to the outer housing 14. Generally, a zero-closure seal can be configured to form a seal in a working channel when no instrument is disposed therethrough to thus prevent the leakage of insufflation gases delivered through the surgical access device to the body cavity. A duckbill seal can generally have opposed flaps that extend at an angle toward one another in a distal direction and that come together at a distal end to form a seal face. The opposed flaps can be movable relative to one another to allow the seal face to move between a closed position, in which no instrument is disposed therethrough and the seal face seals the working channel of the surgical access device, and an open position in which an instrument is disposed therethrough. A duckbill seal can include various other features, as described in more detail in U.S. application Ser. No. 11/771,263, entitled "Duckbill Seal with Fluid Drainage Feature," filed on Jun. 29, 2007, which is hereby incorporated by reference in its entirety. In addition, the seal face of the duckbill seal can be in any nonlinear shape or configuration known in the art, for example in an S-shaped configuration, as described in more detail in U.S. Pat. No. 5,330,437, entitled "Self Sealing Flexible Elastomeric Valve and Trocar Assembly for Incorporating Same," filed Nov. 12, 1993, which is hereby incorporated by reference in its entirety.

As mentioned above, the sealing ports 22a, 22b, 22c can be configured to be in a fixed position relative to their respective housing portions 24a, 24b, 24c and to move with their respective housing portions 24a, 24b, 24c relative to the outer housing 14 and the retractor 18, as discussed further below. However, any one or more of the sealing ports 22a, 22b, 22c can be configured to be movable relative to any one or more portions of the housing 12, such as the housing portions 24a, 24b, 24c, the outer housing 14, or any others of the sealing ports 22a, 22b, 22c.

Figure 10:
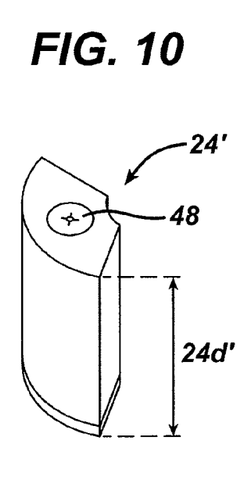
FIG. 10 is a perspective view of one embodiment of a discrete housing portion.
Figure 11:
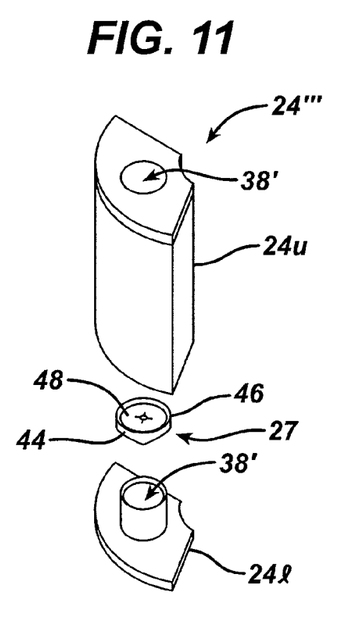
FIG. 11 is an exploded view of the discrete housing portion of FIG. 10.
Figure 12:
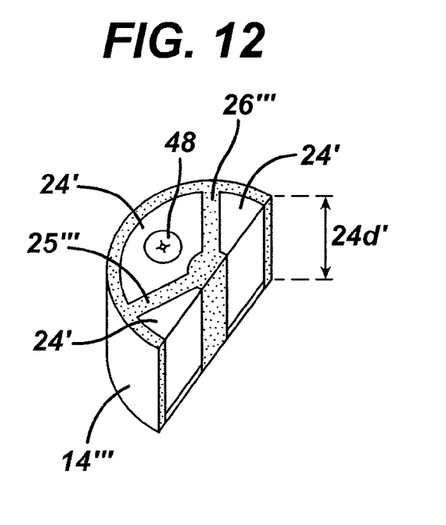
FIG. 12 is a perspective, cross-sectional view of one embodiment of a surgical access device including a plurality of the discrete housing portions of FIG. 10.

As shown in FIGS. 4 and 7, the sealing elements can distally extend from their respective housing portions 24a, 24b, 24c, and from the flexible member 26, such that at least distal portions of the sealing elements freely extend into the working channel 14a of the outer housing 14. Such a configuration can facilitate movement of the housing portions 24a, 24b, 24c and the sealing elements relative to the outer housing 14 and help better position instruments inserted through the housing portions 24a, 24b, 24c. However, in some embodiments one or more of the housing portions can be configured such that the sealing elements can be contained therein. In an exemplary embodiment illustrated in FIGS. 10-12, a discrete housing portion 24' can include a wedge-shaped block having a depth 24d' equal to (as shown) or less than a depth of an outer housing 14''' in which it is disposed. In this way, a flexible member 26''' disposed in the outer housing 14''' and surrounding multiple ones of the housing portions 24' disposed therein can fill channels 25''' defined by the housing portions 24' disposed in a working channel of the outer housing 14''' such that the outer housing's working channel includes no open space, e.g., is filled by the flexible member 26''' and the housing portions 24'. The housing portions 24' can each include an upper portion 24u matable to a lower portion 24l in a fluid-tight mating connection with a sealing element 27 including the duckbill seal 44, the septum seal 46, and the protective member 48 of FIG. 8 disposed in an opening 38' defined by the upper and lower portions 24u, 24l.

Figure 13:
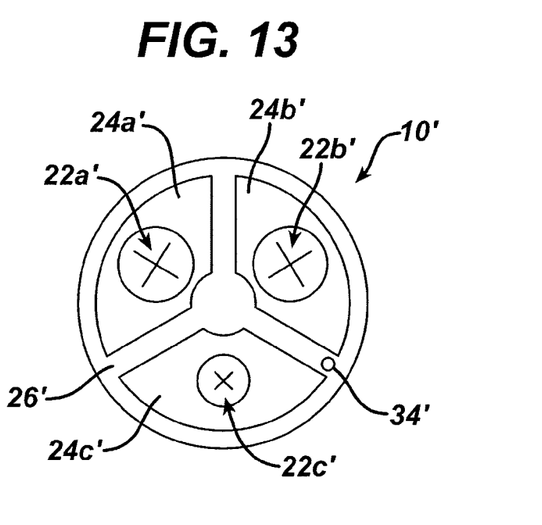
FIG. 13 is a top view of another embodiment of a surgical access device including a plurality of discrete housing portions.
Figure 14:
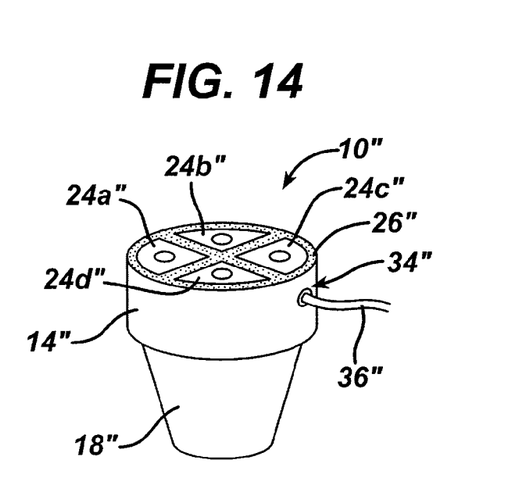
FIG. 14 is a perspective view of one embodiment of a surgical access device including a plurality of discrete housing portions and a rigid retractor.

Although three housing portions 24a, 24b, 24c are shown in the embodiment of FIGS. 1-4, the device 10 can include any number of discrete housing portions. The illustrated housing portions 24a, 24b, 24c are identical, but a person skilled in the art will appreciate that any one or more of the housing portions 24a, 24b, 24c can be different from any one or more of the device's other housing portions 24a, 24b, 24c. FIG. 13 illustrates an exemplary embodiment of a surgical access device 10' including three discrete wedge-shaped housing portions 24a', 24b', 24c' in which two of the housing portions 24a', 24b' have sealing ports 22a', 22b' of a first size, e.g., 7 mm, and the other housing portion 24c' has a second, smaller size, e.g., 3 mm. Providing different sealing port sizes 22a', 22b', 22c' can help facilitate insertion of differently sized surgical instruments through the device 10' and effectively seal the instruments inserted therethrough. The device 10' also includes an insufflation port 34' extending from a flexible member 26' disposed between the housing portions 24a', 24b', 24c'. FIG. 14 illustrates another exemplary embodiment of a surgical access device 10" including four discrete wedge-shaped housing portions 24a", 24b", 24c", 24d" and having an insufflation port 34" extending from a sidewall of an outer housing 14" in which the housing portions 24a", 24b", 24c", 24d" are disposed. The insufflation port 34" can be configured to couple to an insufflation tube 36". FIG. 14 also illustrates an exemplary embodiment of a rigid retractor 18" distally extending from the outer housing 14" and having a distally-tapering truncated cone shape. FIG. 15 illustrates an exemplary embodiment of a discrete housing portion 24''' having an insufflation port 34''' extending proximally therefrom, although the insufflation port 34''' can extend therefrom in any direction.

As surgical instruments are inserted through the surgical access device embodiments described herein, a risk can exist that a particularly sharp instrument may tear or puncture a portion of the retractor or nearby tissue. Accordingly, in any and all of the embodiments described herein, a retractor protector or safety shield can optionally be included to reduce the risk of tearing or puncture by a surgical instrument. In an exemplary embodiment, a retractor protector can be configured to extend at least partially into the inner lumen 18a of the retractor 18 to thereby provide a protective lining as surgical instruments are inserted through the device 10. The retractor protector can have a length corresponding to a length of the retractor 18, but can also have a length less than or considerably longer than the length of the retractor 18 depending on a specific application. The retractor protector can be mated to the device's proximal portion 16, e.g., the housing 12, using any attachment mechanism, e.g., adhesive, screws, press fit, etc., as will be appreciated by a person skilled in the art. In general the retractor protector can be of a material that is relatively smooth and with a low coefficient of friction to allow ease of passage of instruments, but resistant to tearing and puncture. For example, the retractor protector can be formed of silicone, urethane, thermoplastic elastomer, rubber, polyolefins, polyesters, nylons, fluoropolymers, and any other suitable materials known in the art. The retractor protector can generally provide a liner for a retractor or tissue and can be detachable from a surgical access device so it can be used as needed in a particular procedure. A retractor protector can include a plurality of layers, or a retractor protector can be a singular member. Exemplary embodiments of retractor protectors are described in more detail in U.S. patent application Ser. No. 12/399,625 entitled "Methods And Devices For Providing Access Into A Body Cavity," filed on Mar. 6, 2009, U.S. Patent Application No. 2006/0247673 entitled "Multi-port Laparoscopic Access Device" filed Nov. 2, 2006, U.S. application Ser. No. 12/399,482 entitled "Methods and Devices for Providing Access to a Body Cavity" filed on Mar. 6, 2009, U.S. application Ser. No. 12/242,765 entitled "Surgical Access Device" filed on Sep. 30, 2008, U.S. application Ser. No. 12/512,542 entitled "Methods And Devices For Providing Access Into A Body Cavity" filed on Jul. 30, 2009, and U.S. application Ser. No. 12/512,568 entitled "Methods And Devices For Providing Access Into A Body Cavity" filed on Jul. 30, 2009, which are hereby incorporated by reference in their entireties.

In use, one or more surgical instruments can be inserted into a body cavity through the surgical access device 10, which can help optimally position the surgical instruments relative to the body cavity through movement of the housing portions 24a, 24b, 24c relative to one another, to the outer housing 14, and to the retractor 18. The device 10 can be positioned within tissue to provide access to a body cavity underlying the tissue in a variety of ways. In an exemplary embodiment, illustrated in FIGS. 16 and 17, the device 10 can be positioned in tissue 58 fully assembled in the device's default position, shown in FIGS. 1 and 2. In another embodiment, the device 10 can be positioned partially assembled in the tissue 58 and be fully assembled with a portion of the device 10 positioned in the tissue 58.

The retractor 18 can be positioned within an opening or incision 60 formed in the tissue 58 (generally referred to as an "opening"), e.g., in the umbilicus, with the proximal and distal flanges 28, 30 of the retractor 18 positioned on opposed sides of the tissue 58. The inner elongate portion 32 of the retractor 18 can thereby be positioned within the tissue 58 with the working channel 18a of the retractor 18 extending through the tissue 58 to provide a path of access to a body cavity 62 underlying the tissue 58. The tissue opening 60 can have any shape and size, e.g., a linear cut having a longitudinal length in a range of about 15 to 35 mm and extending through a layer of tissue having a depth of less than about 70 mm. The retractor 18 can be positioned within the tissue opening 60 in a variety of ways. In an exemplary embodiment, the retractor 18 can be positioned in the opening 60 by hand. In another exemplary embodiment, the retractor 18 can be positioned in the opening 60 using an inserter tool (not shown). Exemplary embodiments of hand-insertion and of an inserter tool are described in more detail in previously mentioned U.S. application Ser. No. 12/512,542 entitled "Methods And Devices For Providing Access Into A Body Cavity" filed on Jul. 30, 2009, and U.S. application Ser. No. 12/512,568 entitled "Methods And Devices For Providing Access Into A Body Cavity" filed on Jul. 30, 2009.

Figure 16:
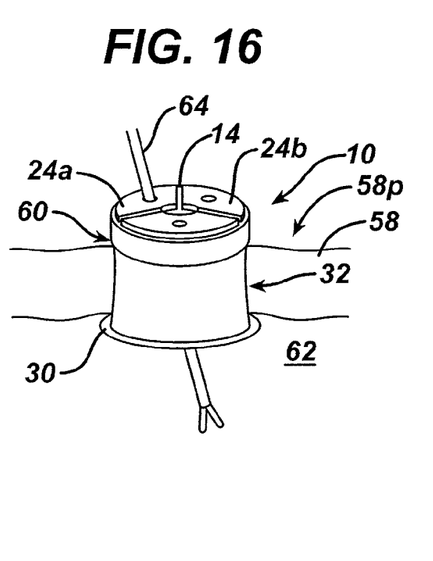
FIG. 16 is a perspective, partially cross-sectional view of the surgical access device of FIG. 1 positioned within a tissue opening and having a surgical instrument inserted through one of the discrete housing portions.
Figure 17:
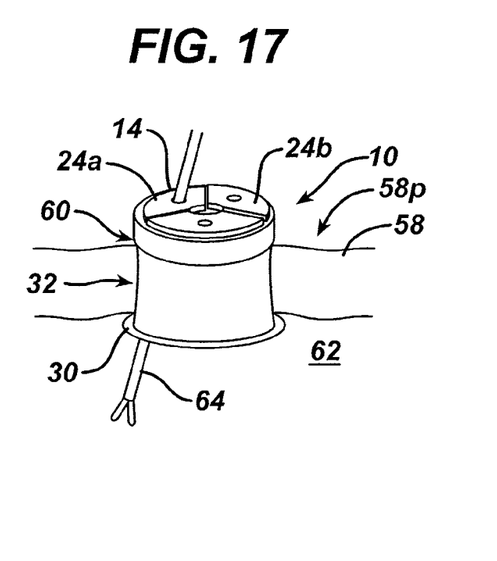
FIG. 17 is a perspective, partially cross-sectional view of the surgical access device of FIG. 16 with the discrete housing portion having the instrument inserted therethrough moved to a different position relative to the other discrete housing portions.
Figure 18:
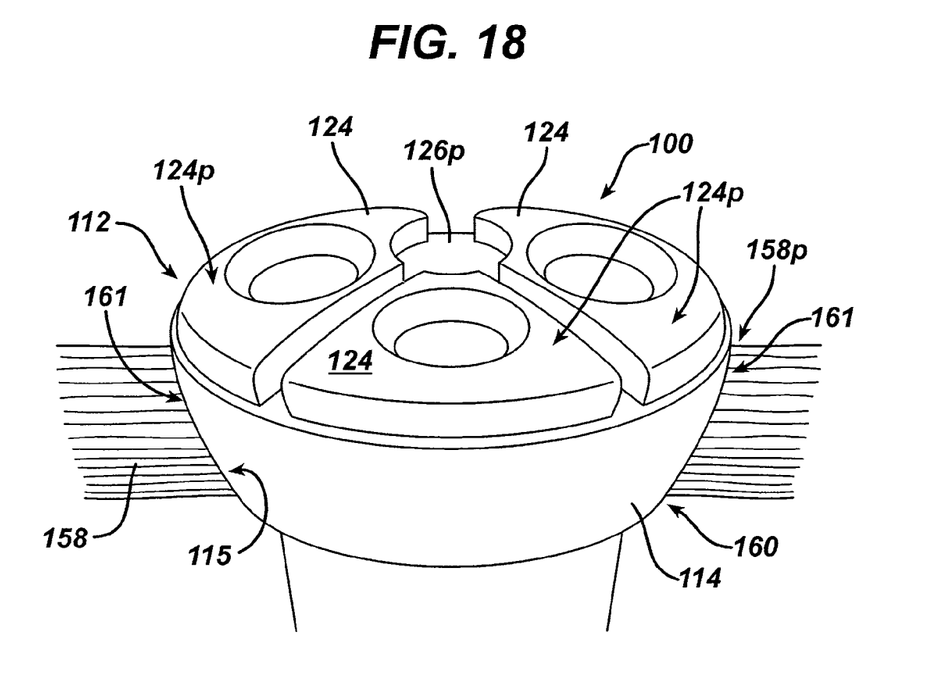
FIG. 18 is a perspective, partially cross-sectional view of another embodiment of a surgical access device having a plurality of discrete housing portions, the surgical access device being positioned within a tissue opening.

As shown in FIGS. 16 and 17, the housing 12 can be positioned above a proximal surface 58p of the tissue 58 such that a distal surface of the housing 12, e.g., a distal surface of the outer housing 14, can abut the tissue's proximal surface 58p. In some embodiments, a housing 112 of a surgical access device 100 can be at least partially disposed in an opening 160 in tissue 158, as shown in an exemplary embodiment in FIG. 18, where a sidewall 115 of an outer housing 114 can be positioned fully or partially in contact with inner walls 161 of the tissue opening 160. With the device 100 including multiple housing portions 124 having proximal surfaces 124p raised above a proximal surface 126p of a flexible member 126 surrounding the housing portions 124, the housing portions 124 can extend above a proximal surface 158p of the tissue 158, thereby facilitating access to housing portions 124 despite the housing 112 being disposed at least partially within the tissue opening 160. Such a low profile device 100 can reduce interference with other aspects of the surgical procedure, such as insufflation, visualization inside and outside the patient, etc. If a housing of a surgical access device is configured to be positioned within a tissue opening to provide a pathway therethrough, the surgical access device can optionally include a retractor extending distally from the housing.

Referring again to FIGS. 16 and 17, with the surgical access device 10 assembled and positioned in the tissue opening 60, one or more surgical instruments can be inserted therethrough and into the body cavity 62 where the instruments can help perform any type of surgical procedure. Prior to insertion of any instruments through the device 10, insufflation can be provided using through an insufflation port. As shown in FIG. 16, an instrument 64 can be inserted through the first housing portion 24a in an initial position with the first housing portion 24a in a first position relative to the outer housing 14 and the other housing portions 24b, 24c. The instrument 64 can be moved from the initial position, shown in FIG. 16, to a working position, shown in FIG. 17, thereby flexing the flexible member 26 and moving the first housing portion 24a from a first position in FIG. 16 to a second, different position in FIG. 17, similar to that discussed above. A person skilled in the art will appreciate that the instrument 64 can have any initial and working positions and that the instrument 64 inserted through the first housing portion 24a can be moved any number of times during a surgical procedure. Although the surgical instrument 64 shown in FIGS. 16 and 17 is a grasper having a pair of distal movable jaws, a person skilled in the art will appreciate that any surgical instrument can be inserted through the device 10. Further, although the instrument 64 is illustrated as being inserted through the first housing portion 24a, instruments can be simultaneously and/or sequentially inserted through any of the housing portions 24a, 24b, 24c.

In an embodiment where the housing 12 is removable from the retractor 18, at any point before, during, or after a surgical procedure, the housing 12 in full or part can be released from the retractor 18, and the retractor 18 can be removed from the tissue 58. With the housing 12 of the device 10 disengaged from the retractor 18 and with the retractor 18 still positioned in the tissue opening 60, the working channel 18a of the retractor 18 can provide access to the body cavity 62 underlying the tissue 58. One or more surgical instruments can be advanced through the working channel 18a, such as a waste removal bag configured to hold waste material, e.g., dissected tissue, excess fluid, etc., from the body cavity 62. The bag can be introduced into the body cavity 62 through the retractor's working channel 18a or other access port. A person skilled in the art will appreciate that one or more surgical instruments can be advanced through the retractor's working channel 18a before and/or after the housing 12 has been attached to the retractor 18.

A surgical drape can optionally be placed over the retractor 18 and the tissue opening 60 during removal of the retractor 18 to help reduce dispersion of bodily fluid outside the surgical space.

As will be appreciated by those skilled in the art, any and all of the embodiments disclosed herein can be interchangeable with one another as needed. For example, an exemplary embodiment of a surgical access device kit can include multiple housings with one or more retractors. Each housing can have different sealing port configurations including different types and numbers of sealing elements, etc. as needed in particular application. For another example, an exemplary embodiment of a surgical access device kit can include multiple modular stopcocks, e.g., an insufflation/vent three-way version, a twist to activate version, a spring loaded version, etc.

A person skilled in the art will appreciate that, while methods and devices are described herein in connection with minimally invasive laparoscopic procedures in the abdominal cavity, the methods and devices can be used in almost any part of a human or animal body and in various other types of surgical procedures. By way of non-limiting example, the devices and methods disclosed herein can be used in the thoracic cavity, pelvic cavity, cranial cavity and/or any of the body's natural orifices and can be used in endoscopic procedures and/or in open surgical procedures.

The embodiments described herein can be used in any known and future surgical procedures and methods, as will be appreciated by those skilled in the art. For example, any of the embodiments described herein can be used in performing a sleeve gastrectomy and/or a gastroplasty, as described in U.S. application Ser. No. 12/242,765 entitled "Surgical Access Device" filed on Sep. 30, 2008; U.S. application Ser. No. 12/242,711 entitled "Surgical Access Device with Protective Element" filed on Sep. 30, 2008; U.S. application Ser. No. 12/242,721 entitled "Multiple Port Surgical Access Device" filed on Sep. 30, 2008; U.S. application Ser. No. 12/242,726 entitled "Variable Surgical Access Device" filed on Sep. 30, 2008; U.S. application Ser. No. 12/242,333 entitled "Methods and Devices for Performing Gastrectomies and Gastroplasties" filed on Sep. 30, 2008; U.S. application Ser. No. 12/242,353 entitled "Methods and Devices for Performing Gastrectomies and Gastroplasties" filed on Sep. 30, 2008; and U.S. application Ser. No. 12/242,381 entitled "Methods and Devices for Performing Gastroplasties Using a Multiple Port Access Device" filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a housing, a retractor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical access device, comprising:
an outer housing having proximal and distal ends with a lumen extending therethrough; and
a plurality of discrete housing portions disposed across the proximal end of the outer housing and spaced a distance apart from one another, each housing portion having an opening extending therethrough and in communication with the lumen in the outer housing, and the plurality of housing portions being coupled by a flexible member such that each housing portion is independently movable relative to one another.

2. The surgical access device of claim 1, wherein each housing portion includes at least one sealing element configured to form at least one of a channel seal when no surgical instrument is disposed therethrough and an instrument seal around a surgical instrument inserted therethrough.

3. The surgical access device of claim 1, wherein each housing portion is movable relative to one another in a plane transverse to a longitudinal axis of the outer housing.

4. The surgical access device of claim 1, wherein each housing portion is independently movable in multiple directions relative to one another.

5. The surgical access device of claim 1, wherein each of the housing portions is substantially rigid.

6. The surgical access device of claim 1, wherein the flexible member comprises a gel.

7. The surgical access device of claim 1, wherein the flexible member comprises a foam.

8. The surgical access device of claim 1, further comprising a retractor configured to attach to and distally extend from the outer housing and to be positioned within an opening in tissue, the retractor having a working channel extending therethrough for forming a pathway through tissue into a body cavity.

9. The surgical access device of claim 8, wherein when the retractor is attached to the outer housing, each of the discrete housing portions is movable relative to the retractor.

10. The surgical access device of claim 8, wherein the retractor comprises a flexible elongate cannula extending between a proximal ring member and a distal ring member.

11. A surgical access device, comprising:
an annular ring defining a lumen;
a plurality of discrete housing portions disposed within the ring and defining channels between each of the housing portions, each housing portion having at least one sealing port configured to receive an instrument inserted therethrough and into the lumen; and
a flexible member disposed in the channels such that each of the housing portions can move relative to one another in a plane transverse to a longitudinal axis of the ring.

12. The surgical access device of claim 11, wherein each sealing port includes at least one sealing element configured to form at least one of a channel seal when no surgical instrument is disposed therethrough and an instrument seal around a surgical instrument inserted therethrough.

13. The surgical access device of claim 11, wherein the channels are configured to prevent any of the housing portions from directly contacting one another.

14. The surgical access device of claim 11, wherein each of the housing portions is in a longitudinally fixed position relative to the annular ring.

15. The surgical access device of claim 11, wherein the flexible member provides a fluid-tight seal for the lumen.

16. The surgical access device of claim 11, further comprising a retractor distally extending from the annular ring and configured to be positioned within an opening in tissue, the retractor having a working channel extending therethrough for forming a pathway through tissue into a body cavity.

* * * * *